(12) United States Patent
Woods

(10) Patent No.: US 6,443,985 B1
(45) Date of Patent: Sep. 3, 2002

(54) INTRAOCULAR LENS IMPLANT HAVING EYE ACCOMMODATING CAPABILITIES

(76) Inventor: Randall Woods, 136 Valley Ranch North, Prescott, AZ (US) 86303

( * ) Notice: Subject to any disclaimer, the term of this patent is extended or adjusted under 35 U.S.C. 154(b) by 0 days.

(21) Appl. No.: 09/940,018

(22) Filed: Aug. 27, 2001

(51) Int. Cl.$^7$ .................................................. A61F 2/16
(52) U.S. Cl. ..................................... 623/6.46; 623/6.11
(58) Field of Search ........................... 623/6.11, 6.38, 623/6.39, 6.41, 6.4, 6.43–6.55, 6.37, 6.13

(56) References Cited

U.S. PATENT DOCUMENTS

| | | | | |
|---|---|---|---|---|
| 5,674,282 A | * | 10/1997 | Cumming | 623/6 |
| 6,152,958 A | * | 11/2000 | Nordan | 623/6.25 |
| 6,299,641 B1 | * | 10/2001 | Woods | 623/6.37 |
| 6,322,589 B1 | * | 11/2001 | Cumming | 623/6.44 |

* cited by examiner

Primary Examiner—Corrine McDermott
Assistant Examiner—Hieu Phan
(74) Attorney, Agent, or Firm—Hovey Williams LLP

(57) ABSTRACT

An improved intraocular lens (28) is provided which more closely mimics the accommodation and focusing of the eye's natural lens. The lens (28) includes a central optic (30) together with a resilient positioning element (38) including a plurality of spaced-apart positioning legs (44) with openings (46) therebetween. The element (38) is configured so that the equatorial segment (48) thereof is maintained in substantial contact with at least a part of the corresponding equatorial portion (27) of the capsule (20), during essentially all orientations of the lens (28) within the capsule (20). A thin membrane (56) may be used to cover the openings (46) to thereby impede the passage of cells into the lens (28).

19 Claims, 2 Drawing Sheets

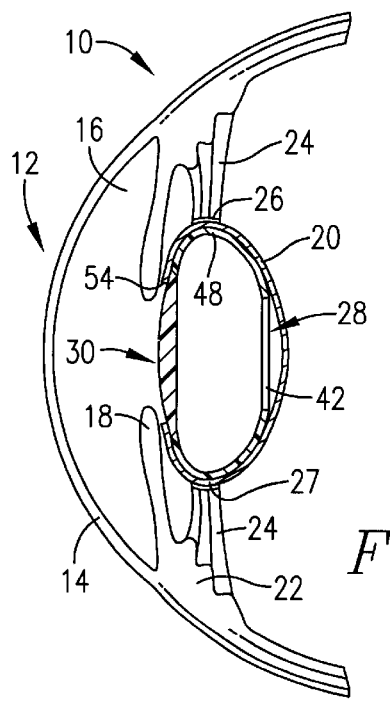
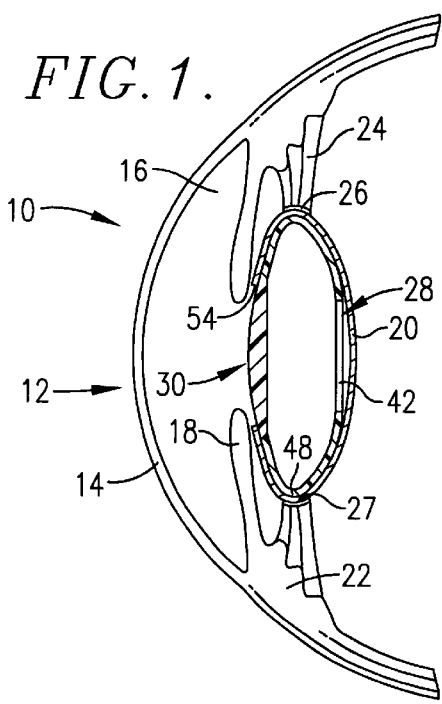
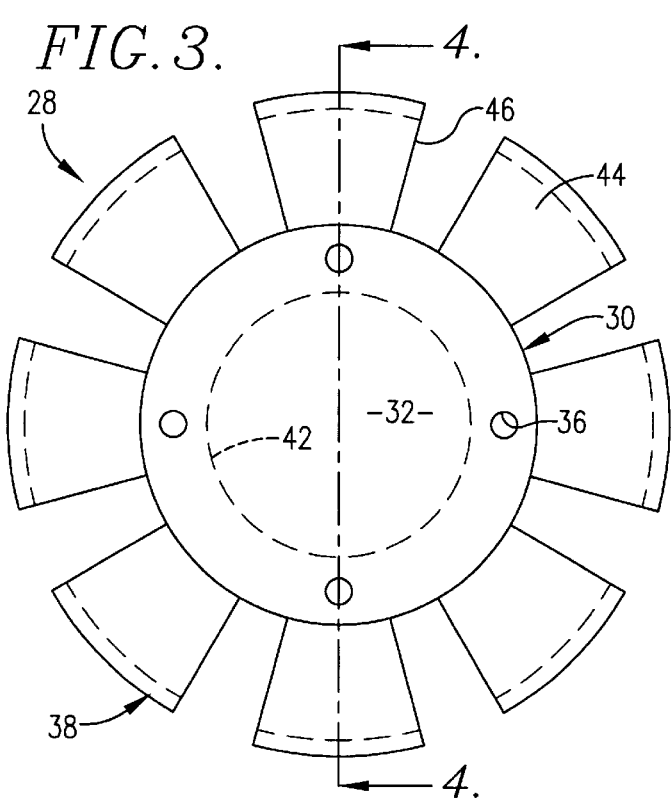
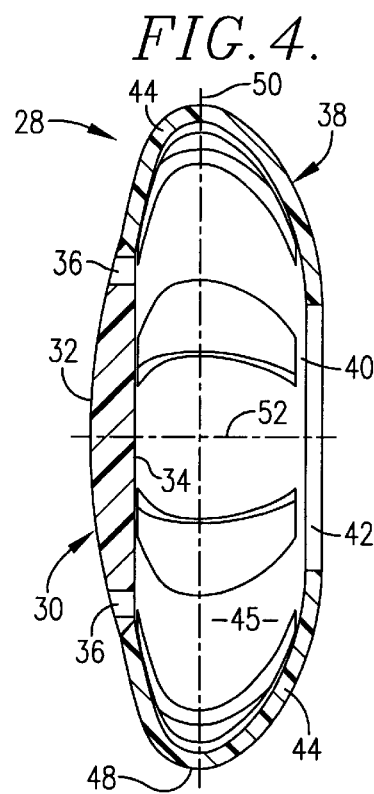

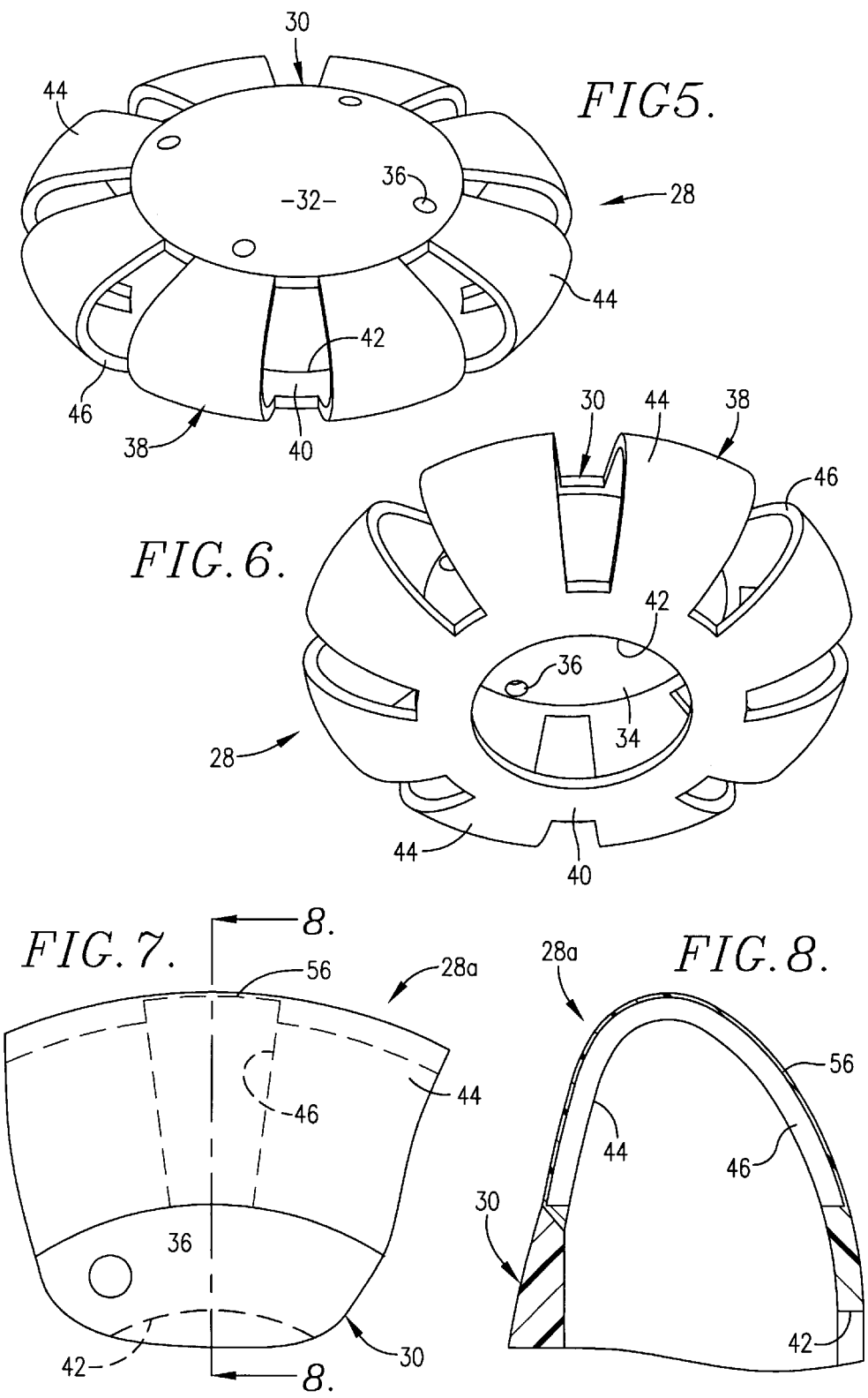

# INTRAOCULAR LENS IMPLANT HAVING EYE ACCOMMODATING CAPABILITIES

BACKGROUND OF THE INVENTION

1. Field of the Invention

The present invention is broadly concerned with improved intraocular lenses which can be surgically implanted as a replacement for the natural crystalline lenses in the eyes of cataract patients. More particularly, the invention is concerned with such intraocular lenses which have a specially configured, resilient optic positioning element serving to maintain the equatorial segment of the positioning element in substantial contact with the corresponding equatorial portion of the capsule of the eye.

2. Description of the Prior Art

Cataracts occur when the crystalline lens of the eye becomes opaque. The cataracts may be in both eyes and, being a progressive condition, may cause fading vision and eventual blindness. Cataracts were once surgically removed along with the anterior wall of the capsule of the eye. The patient then wore eyeglasses or contact lenses which restored vision but did not permit accommodation and gave only limited depth perception.

The first implant of a replacement lens within the eye occurred in 1949 and attempted to locate the replacement lens in the posterior chamber of the eye behind the iris. Problems such as dislocation after implantation forced abandonment of this approach, and for some period thereafter intraocular lenses were implanted in the anterior chamber of the eye.

Others returned to the practice of inserting the lens in the area of the eye posterior to the iris, known as the posterior chamber. This is the area where the patient's natural crystalline lens is located. When the intraocular lens is located in this natural location, substantially normal vision may be restored to the patient and the problems of forward displacement of vitreous humor and retina detachment encountered in anterior chamber intraocular lenses are less likely to occur. Lenses implanted in the posterior chamber are disclosed in U.S. Pat. Nos. 3,718,870, 3,866,249, 3,913,148, 3,925,825, 4,014,049, 4,041,552, 4,053,953, and 4,285,072. None of these lenses have focusing capability.

Lenses capable of focusing offered the wearer the closest possible substitute to the crystalline lens. U.S. Pat. No. 4,254,509 to Tennant discloses a lens which moves in an anterior direction upon contraction of the ciliary body located anterior to the iris. Though providing focusing capabilities, it presents the same disadvantages as other anterior chamber lenses. U.S. Pat. No. 4,253,199 to Banko approaches the problem of providing a focusable lens differently, by providing a replacement lens of deformable material sutured to the ciliary body. This lens functions much as the original crystalline lens but risks bleeding from the sutures.

U.S. Pat. No. 5,674,282 to Cumming is directed towards an accommodating intraocular lens for implanting within the capsule of an eye. The Cumming lens comprises a central optic and two plate haptics which extend radially outward from diametrically opposite sides of the optic and are movable anteriorly and posteriorly relative to the optic. However, the Cumming lens suffers from the same shortcomings as the Levy lens in that the haptics are biased anteriorly by pressure from the ciliary bodies. This will eventually lead to pressure necrosis of the ciliary body.

Finally, U.S. Pat. No. 4,842,601 to Smith discloses an accommodating intraocular lens having anterior and posterior members which urge against the anterior and posterior walls of the natural lens capsule. The muscular action exerted on the natural capsule will thus cause the lens to flatten, thereby changing the focus thereof. The Smith lens is formed of first and second plastic lens members connected to one another adjacent their peripheral edges so as to provide a cavity therebetween. The connection between the lens members is accomplished by way of a U-shaped flange on the first member which forms an inwardly facing groove for receiving an outwardly extended flange on the second member. The Smith lens is lacking in that the first and second members must be separately inserted into the capsule and assembled within the capsule which is extremely difficult for even highly skilled surgeons to accomplish.

SUMMARY OF THE INVENTION

The present invention represents a significant advance in the art and provides an accommodating intraocular lens for implantation substantially within the confines of the capsule of the human eye between the anterior and posterior capsule walls. The lens comprises a single optic presenting opposed anterior and posterior surfaces, together with a resilient optic positioning element coupled to the optic to cooperatively present a shape that generally conforms to the shape of the capsule. The optic positioning element has a posterior face configured for yieldable engagement with the posterior capsule wall, and an anterior face configured for yieldable engagement with the anterior wall of the capsule. The positioning element also defines an equatorial segment of maximum diameter between the anterior and posterior faces. The positioning element is operable to substantially maintain the equatorial segment thereof in contact with at least a part of the capsule equatorial portion in essentially all orientations and conditions of accommodation of the lens within the capsule.

The positioning element is preferably formed of a yieldable synthetic resin material to present a unitarily formed, seamless body having an elastic memory. In practice, the lens of the invention is surgically implanted within a capsule, so as to take full advantage of the "rubber band effect." This in turn assures accurate lens accommodation in response to contraction and relaxation of the ciliary body, acting through the zonules and the elastin tissue of the eye.

BRIEF DESCRIPTION OF THE DRAWINGS

FIG. 1 is a generally schematic vertical sectional view of an intraocular lens in accordance with the invention, shown mounted in the capsule of an eye;

FIG. 2 is a view similar to that of FIG. 1, but illustrating the intraocular lens in an accommodated position owing to relaxation of the ciliary muscle;

FIG. 3 is a plan view of a preferred lens of the invention;

FIG. 4 is a vertical sectional view taken along line 4—4 of FIG. 3 and further illustrating the construction of the intraocular lens;

FIG. 5 is a top perspective view of the lens of FIG. 3;

FIG. 6 is a bottom perspective view of the lens of FIG. 3;

FIG. 7 is an enlarged, fragmentary view of another embodiment in accordance with the invention, including a thin membrane in covering relationship to openings present in the optic positioning element to impede migration of cells therethrough; and FIG. 8 is a vertical sectional view taken along line 8—8 of FIG. 7 and further depicting the construction of the FIG. 7 embodiment.

DETAILED DESCRIPTION OF THE PREFERRED EMBODIMENT

Turning now to the drawings, the present invention provides an intraocular lens for surgical replacement of the human lens in the treatment of cataracts in the human eye. FIGS. 1 and 2 illustrate various components of the human eye. Briefly, the eye 10 includes a frontal portion 12 and a rearward portion including the retina (not shown). The frontal portion 12 of the eye 10 is covered by a cornea 14 which encloses and forms an anterior chamber 16. The anterior chamber 16 contains aqueous fluid and is bounded at the rear by an iris 18. The iris 18 opens and closes to admit appropriate quantities of light into the inner portions of the eye 10. The eye 10 also includes a capsule 20 which ordinarily contains the natural crystalline lens. When the eye 10 focuses, the capsule 20 changes shape to appropriately distribute the light admitted through the cornea 14 and the iris 18 to the retina at the rearward portion of the eye 10.

The capsule 20 is supported within eye 10 by means of the ciliary muscle 22 which supports zonules 24, the latter including elastin tissue substantially about the equatorial portion 27 of the capsule 20.

The retina is composed of rods and cones which act as light receptors. The retina includes a fovea which is a rodless portion that provides for acute vision. The outside of the rearward or posterior portion 14 of the eye 10 is known as the sclera which joins into and forms a portion of the covering for the optic nerve. Images received by the retina are transmitted through the optic nerve to the brain. The area between the retina and the capsule 20 is occupied by vitreous fluid.

Ocular adjustments for sharp focusing of objects viewed at different distances is accomplished by the action of the ciliary body 22 on the capsule 20 and the naturally occurring crystalline lens. This is accomplished through the zonules 24 and the elastin tissue 26 forms a part thereof creating a so-called "rubber band effect." For example, when the ciliary body 22 contracts, the zonules 24 and elastin tissue 26 exerts forces on the capsule 20 to achieve a more spherical shape as shown in FIG. 2 for viewing objects that are nearer the viewer. When the ciliary body 22 retracts and pulls on the zonules 24, a force is exerted in an opposite direction to make the capsule 20 more discoid; objects at a distance can then be viewed in proper focus.

Referring now to FIGS. 3–6, a preferred intraocular lens (IOL) 28 is illustrated. The IOL 28 includes a central optic 30 which may be formed of an acrylic or similar synthetic resin material and presents an anterior surface 32 and an opposed posterior surface 34. The surfaces 32, 34 are normally convex, although the shape of these surfaces and the overall size of the optic 30 an be varied depending upon the user's eyesight. The optic 30 is also provided with four circumferentially spaced through-openings 36.

The IOL 28 further includes a resilient positioning element 38 which serves to locate the optic 30 within a human capsule 20 and to effect accommodation of the lens. The element 38 may be integral with optic 30 or may be structurally distinct; in either case the element 38 is preferably unitarily formed as a seamless component. As illustrated, the element 38 includes an annular posterior segment 40 with a central opening 42. A plurality of circumferentially spaced, arcuate in cross-section positioning legs 44 extend from the segment 42 and are joined to the margin of optic 30, with openings 46 defined between adjacent pairs of the legs 44. As perhaps best seen in FIG. 4, the legs 44 cooperatively present, with the optic 30, a substantially discoid shape with a central chamber 45. However, the legs 44 also define an annular equatorial segment 48 disposed on opposite sides of equatorial axis 50 (FIG. 4). The overall IOL further presents a central polar axis 52 as shown. Preferably, the outside dimension of the IOL 28 at the equatorial segment 48 is from about 9–11 mm, usually about 10 mm. On the other hand, the outside dimension along polar axis 52 is typically from about 2–4 mm, usually about 3 mm.

The positioning element 38 is preferably formed of any appropriate biologically inert material conventionally used in IOL construction (e.g., elastic, synthetic resin materials). Examples of suitable lens materials include acrylates (such as polymethylmethacrylates), silicones, and mixtures of acrylates and silicons. It is particularly preferred that lenses according to the invention be constructed of a material having an elastic memory (i.e., the material should be capable of substantially recovering its original size and shape after a deforming force has been removed). An example of a preferred material having elastic memory is MEMORYLENS (available from Mentor Ophthalmics in California).

A particular feature of IOL 28 is that the positioning element 38 thereof is configured so as to substantially conform with the capsule 20, particularly to the equatorial portion 27 of the capsule. This is shown in FIGS. 1 and 2, where it will be observed that the equatorial segment 48 of the IOL 28 is in substantially conforming contact with the inner surface of the equatorial portion 27 of capsule 20. Note also that this close conforming relationship is maintained notwithstanding the extent of accommodation of the lens 28. In this fashion, the lens 28 makes full use of the "rubber band effect" of the natural eye 10, and thus more closely mimics accommodation of the eye's natural lens.

Intraocular lens 28 substitutes both locationally and functionally for the original, natural, crystalline lens. In order to insert the lens 28 into the capsule 20, an ophthalmic surgeon would remove the natural lens (and thus the cataracts) by conventional methods, leaving an opening 54 in the anterior wall of the capsule 20. Lens 28 is then folded into a compact size for insertion into the capsule 20 through the opening 54. Once inserted, the capsule 20 is filled with fluids (e.g., saline solution) which enter the lens 28, causing the lens 38 to return to its original, non-deformed state as shown in FIG. 1. There is no need to suture the lens to the capsule 20 because, due to the size and shape of the lens 28 as described above, the lens 28 will not rotate or shift within the capsule 20.

Implantation of the IOL 28 restores normal vision because, not only does the lens 28 replace the patients occluded natural lens, but the normal responses of the ciliary body 22 cooperate with the zonules 24 and elastin tissue 26 during focusing of the lens 28. In FIG. 2, the focal length between the posterior surface 34 of optic 30 and the fovea is greater to permit viewing of nearby objects. The focal length is greater because the ciliary muscle or body 22 has contracted, making the capsule 20 more spheroid; this causes the lens 28 to be maintained in its tensioned state, positioning the optic 30 anteriorly. The lens 28 thus follows the eye's natural physiology for focusing to provide a substitute means of optical accommodation. When the object of observation becomes more distant, the sensory cells within the retina signal the ciliary body 22 to relax, thus pulling on the zonular fibers 24 to make the capsule more discoid as shown in FIG. 1. In so doing, the polar dimension of the capsule 20 is narrowed, which in turn causes the polar dimension of the lens 28 to narrow in a similar manner. This narrowing causes the optic 30 to move posteriorly as the capsule 20 and the lens 28 become more discoid. The focal length between the posterior surface 34 of optic 30 and the fovea is thus shortened, and the object remains in focus.

FIGS. 7 and 8 illustrate a modified IOL 28a which is identical in all respects with IOL 28, save for the provision of a very thin membrane 56 in covering relationship to the openings 46 between positioning legs 44. It is contemplated that the membrane 56 would be formed of the same synthetic resin as the positioning element 38, but would be much thinner (on the order of a few thousandths of an inch) than the remainder of the element 38. The purpose of membrane 56 is to prevent or at least impede the passage of migratory cells through the openings 46 and into the chamber 45 of the IOL.

The subject matter of U.S. Pat. No. 6,217,612 issued Apr. 17, 2001, and the subject matter of U.S. patent application Ser. No. 09/656,797, filed Sep. 7, 2000, are incorporated by reference herein.

I claim:

1. An accommodating intraocular lens for implantation substantially within the confines of the capsule of a human eye between the anterior and posterior capsule walls, there being zonule elastin tissue disposed about the equatorial portion of said capsule, said lens comprising:

a single optic presenting an anterior surface; and a resilient optic positioning element coupled to the optic to cooperatively present a shape that generally conforms to the shape of the capsule, said optic positioning element presenting a posterior face that is configured for yieldable engagement with the posterior capsule wall, an anterior face configured for yieldable engagement with the anterior wall of the capsule, and an equatorial segment between said posterior and anterior faces, said optic positioning element operable to substantially maintain the equatorial segment thereof in contact with at least a portion of said capsule equatorial portion in essentially all orientations of said lens within said capsule.

2. The lens of claim 1, said optic positioning element comprising a seamless body.

3. The lens of claim 1, said optic presenting a convex anterior surface.

4. The lens of claim 1, said optic positioning element being formed of a yieldable synthetic resin material.

5. The lens of claim 1, said optic positioning element being formed of a synthetic resin elastic material.

6. The lens of claim 5, said material comprising a material selected from the group consisting of silicones, acrylics, and mixtures thereof.

7. The lens of claim 1, wherein said optic positioning element is formed of a material having an elastic memory.

8. The lens of claim 1, said anterior capsule wall having an opening therethrough, said opening and said optic having respective diameters, said optic diameter being greater than said capsule wall opening diameter.

9. The lens of claim 1, wherein said optic positioning element posterior face, said optic positioning element anterior face, and the remainder of the positioning element cooperatively form a chamber within said optic positioning element.

10. The lens of claim 9, wherein said optic positioning element posterior face includes an opening therethrough, said opening communicating with said chamber.

11. The lens of claim 1, said optic positioning element being unitarily formed.

12. The lens of claim 1, said optic positioning element having a series of spaced apart opening formed therein.

13. The lens of claim 12, said openings being uniformly spaced about said optic.

14. The lens of claim 12, including a thin cover disposed over said openings and operable to impede the migration of cells through said openings.

15. The lens of claim 1, including at least one opening through said optic.

16. The lens of claim 1, the outside diameter of said equatorial segment being from about 9–11 mm.

17. The lens of claim 16, the outside polar dimension of said lens being from about 2–4 mm.

18. The lens of claim 1, said optic being formed of any acrylic material, said optic positioning element being formed of a silicone material.

19. An accommodating intraocular lens for implantation substantially within the confines of the capsule of a human eye between the anterior and posterior capsule walls, there being zonule elastin tissue disposed about the equatorial portion of said capsule, said lens comprising:

a single optic presenting an anterior surface; and a resilient optic positioning element coupled to the optic to cooperatively present a shape that generally conforms to the shape of the capsule, said optic positioning element presenting a posterior face that is configured for yieldable engagement with the posterior capsule wall, an anterior face configured for yieldable engagement with the anterior wall of the capsule, and an equatorial segment between said posterior and anterior faces, said optic positioning element operable to substantially maintain the equatorial segment thereof in contact with at least a portion of said capsule equatorial portion in essentially all orientations of said lens within said capsule, said optic and said optic positioning element cooperatively forming a chamber, said optic positioning element posterior face including an opening therethrough communicating with said chamber, the outside diameter of said equatorial segment being from about 9–11 mm, the outside polar dimension of said lens being from about 2–4 mm.

\* \* \* \* \*